(12) United States Patent
Yamaguchi et al.

(10) Patent No.: US 9,951,094 B2
(45) Date of Patent: Apr. 24, 2018

(54) PHOSPHOLE COMPOUND AND FLUORESCENT DYE CONTAINING THE SAME

(71) Applicant: NATIONAL UNIVERSITY CORPORATION NAGOYA UNIVERSITY, Nagoya-shi, Aichi (JP)

(72) Inventors: Shigehiro Yamaguchi, Nagoya (JP); Aiko Fukazawa, Nagoya (JP); Eriko Yamaguchi, Nagoya (JP); Chenguang Wang, Nagoya (JP)

(73) Assignee: NATIONAL UNIVERSITY CORPORATION NAGOYA UNIVERSITY, Nagoya (JP)

( * ) Notice: Subject to any disclaimer, the term of this patent is extended or adjusted under 35 U.S.C. 154(b) by 0 days.

(21) Appl. No.: 15/112,499

(22) PCT Filed: Jan. 22, 2015

(86) PCT No.: PCT/JP2015/051636
§ 371 (c)(1),
(2) Date: Jul. 19, 2016

(87) PCT Pub. No.: WO2015/111647
PCT Pub. Date: Jul. 30, 2015

(65) Prior Publication Data
US 2016/0333037 A1    Nov. 17, 2016

(30) Foreign Application Priority Data

Jan. 24, 2014 (JP) ................................ 2014-011473

(51) Int. Cl.
| | | |
|---|---|---|
| C07F 9/6568 | (2006.01) |
| C09K 11/06 | (2006.01) |
| C09B 57/00 | (2006.01) |
| H01L 51/00 | (2006.01) |
| C09B 69/10 | (2006.01) |
| H01L 51/50 | (2006.01) |

(52) U.S. Cl.
CPC .......... *C07F 9/65685* (2013.01); *C09B 57/00* (2013.01); *C09B 57/008* (2013.01); *C09B 69/10* (2013.01); *C09K 11/06* (2013.01); *H01L 51/0061* (2013.01); *H01L 51/0071* (2013.01); *H01L 51/0072* (2013.01); *C09K 2211/1007* (2013.01); *C09K 2211/1011* (2013.01); *C09K 2211/1014* (2013.01); *C09K 2211/1029* (2013.01); *C09K 2211/1096* (2013.01); *H01L 51/5012* (2013.01)

(58) Field of Classification Search
CPC ... C07F 9/65685; C09B 57/008; C09B 69/10; C09K 11/06
USPC .......................................................... 546/23
See application file for complete search history.

(56) References Cited

U.S. PATENT DOCUMENTS

2010/0253212 A1    10/2010   Cheng et al.

FOREIGN PATENT DOCUMENTS

JP    2012-191031 A    10/2012

OTHER PUBLICATIONS

Jul. 28, 2016 International Preliminary Report on Patentability issued in Patent Application No. PCT/JP2015/051636.
Mar. 10, 2015 International Search Report issued in International Patent Application No. PCT/JP2015/051636.
Yoshihiro Matano et al. "Synthesis of 2-Alkenyl- and 2-Alkynyl-Benzo [b] Phospholes by Using Pallladium-Catalyzed Cross-Coupling Reactions". Organic Letters, 2013, vol. 15, No. 17, pp. 4458-4461.
Aiko Fukazawa et al. "Benzo[b]Phosphole-Containing p-Electron Systems: Synthesis Based on an Intramolecular Trans-Halophosphanylation and Some Insights Into Their Properties". Chemistry, An Asian Journal, 2009, vol. 4, pp. 1729-1740.
Yuto Unoh et al. "An Approach to Benzophosphole Oxides Through Silver- or Manganese-Mediated Dehydrogenative Annulation Involving C-C and C-P Bond Formation". Angewandte Chemie, International Edition, 2013, vol. 52, No. 49, pp. 12975-12979.

(Continued)

*Primary Examiner* — Rita J Desai
(74) *Attorney, Agent, or Firm* — Oliff PLC

(57) ABSTRACT

The following formula is an example of a phosphole compound of the present invention. The phosphole compound of the present invention has the characteristic of maintaining a high fluorescence quantum yield in a wide range of solvents from low-polarity solvents to high-polarity solvents, as well as the characteristic in which the fluorescence wavelength shifts to the longer wavelength side as the polarity of the solvent increases. Because of these characteristics, the phosphole compound of the present invention is expected to be used, for example, for quantitatively determining the polarity in the environment therearound by using the absorption wavelength and fluorescence wavelength thereof, or used as a new fluorescent probe dye or a highly efficient luminescent material in organic electronic devices.

[Chem. 1]

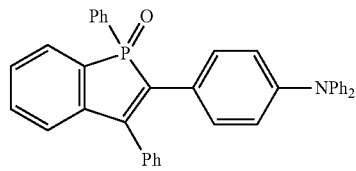

4 Claims, 1 Drawing Sheet

(56) References Cited

OTHER PUBLICATIONS

Katsuaki Baba et al. "Palladium-Catalyzed Direct Synthesis of Phosphole Derivatives From Triarylphosphines Through Cleavage of Carbon-Hydrogen and Carbon-Phosphorus Bonds". Angewandte Chemie, International Edition, 2013, vol. 52, No. 45, pp. 11892-11895.
Leon D. Freedman et al. "Preparation and Ultraviolet Absorption Spectra of Some Derivatives of Phosphafluorinic Acid". Journal of Organic Chemistry, 1959, vol. 24, pp. 638-641.
Jun. 27, 2017 Search Report issued in European Patent Application No. 15741089.5.
Quin, Louis D. et al., "Synthesis of 1,2-Dihydro-1-Phenylindeno[2,1-b]-Phosphole as a Potential Precursor of a Phosphapentalenyl Anion," Tetrahedron, 1983, vol. 39, No. 3, pp. 401-407.

PHOSPHOLE COMPOUND AND FLUORESCENT DYE CONTAINING THE SAME

TECHNICAL FIELD

The present invention relates to a phosphole compound and a fluorescent dye containing the same.

BACKGROUND ART

Fluorescent organic compounds are important chemicals used as a luminescent material of organic light-emitting diodes and a fluorescent dye for biological fluorescence imaging. Therefore, numerous fluorescent organic compounds have been reported in the field of both basic and applied researches. In particular, dyes (for example, acrylodan) whose fluorescent color dramatically changes depending on the surrounding environment are practically used as fluorescent probes for site-specific visualization. It is often reported that the molecular design of combining a highly electron-donating (donor type) π-conjugated unit with a highly electron-accepting (acceptor type) π-conjugated unit is effective in obtaining such fluorescent characteristics. The luminescent color, luminescence efficiency of a fluorescent dye, and the degree of solvent effect highly depend on the choice of π-conjugated units as the donor and the acceptor. Recently, phosphole compounds have been attracting attention as a new type of electron-accepting π-conjugated unit. For example, NPL 1 reports synthesis examples of 2-alkenyl-benzo[b]phosphole oxide and 2-alkynyl-benzo[b]phosphole oxide and optical data thereof. Also, NPL 2 reports synthesis examples of 2-aryl-benzo[b]phosphole oxide and the electrochemical properties thereof. The following are examples of the compounds described in NPLs 1 and 2:

[Chem. 1]

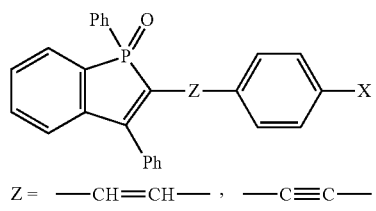

[NPL 1]

Z = —CH=CH—, —C≡C—
X = OMe, H, Cl

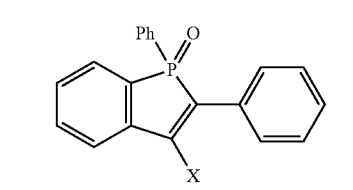

[NPL 2]

X = Cl, Br, H

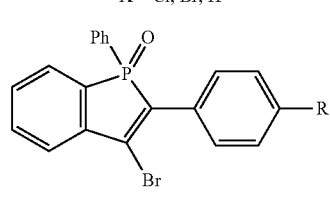

R = Me, OMe, CF$_3$, NMe$_2$

CITATION LIST

Non-Patent Literature

[NPL 1] Organic Letters, 2013, vol. 15, No. 17, p 4458-4461
[NPL 2] Chem. Asian J., 2009, vol. 4, p 1729-1740

SUMMARY OF INVENTION

Technical Problem

Many of the known compounds whose fluorescent color dramatically changes depending on the polarity of the solvent exhibit strong fluorescence in low-polarity solvents, but do not in highly polar protic solvents such as alcohols. Accordingly, it has been desired to develop an environmentally responsive fluorescent compound having novel optical characteristics.

The present invention is intended to solve this issue, and a major object of the invention is to provide a phosphole compound having novel optical characteristics.

Solution to Problem

To solve the above issue, the present inventors synthesized a variety of new phosphole compounds, examined their optical characteristics, and accomplished the present invention by finding that some of the phosphole compounds exhibit novel optical characteristics.

More specifically, the phosphole compound of the present invention is represented by the following formula (1) or formula (2):

[Chem. 2]

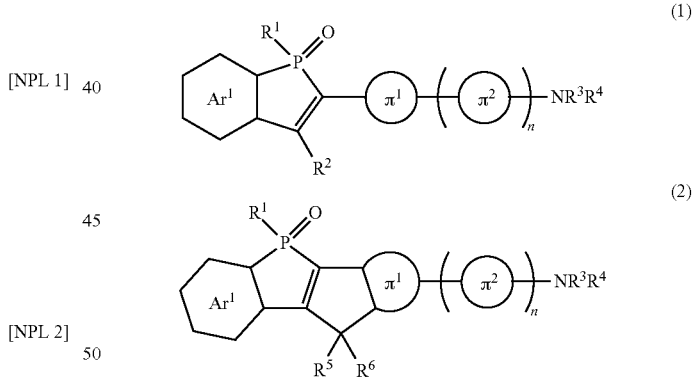

In formula (1), $R^1$ represents an alkyl group, a substituted alkyl group, an aryl group, a substituted aryl group, an alkoxy group, a hydroxy group, an amino group, or a substituted amino group. $R^2$ represents a hydrogen atom, an alkyl group, a substituted alkyl group, an aryl group, a substituted aryl group, a carbonyl group, an imino group, a cyano group, or a fluorine atom. $R^3$ and $R^4$ may be the same or different and are each a hydrogen atom, an alkyl group, a substituted alkyl group, an aryl group, or a substituted aryl group. Ar represents a hydrocarbon aromatic ring, a substituted hydrocarbon aromatic ring, a heteroaromatic ring, or a substituted heteroaromatic ring. n represents 0 or 1. $\pi^1$ and $\pi^2$ represent π-conjugated units that may be the same or different and are each a divalent alkenyl group, a substituted divalent alkenyl group, a divalent alkynyl group, a substituted divalent alkynyl group, a divalent hydrocarbon aromatic ring, a substituted divalent hydrocarbon aromatic ring, a divalent heteroaromatic ring, or a substituted divalent heteroaromatic ring. —NR$^3$R$^4$ is bound to the position of $\pi^1$ or $\pi^2$ at which electrons can be donated to the phosphole skeleton.

In formula (2), R$^1$ represents an alkyl group, a substituted alkyl group, an aryl group, a substituted aryl group, an alkoxy group, a hydroxy group, an amino group, or a substituted amino group. R$^3$ and R$^4$ may be the same or different and are each a hydrogen atom, an alkyl group, a substituted alkyl group, an aryl group, or a substituted aryl group. R$^5$ and R$^6$ may be the same or different and are each a hydrogen atom, an alkyl group, a substituted alkyl group, an aryl group, or a substituted aryl group. Ar represents a hydrocarbon aromatic ring, a substituted hydrocarbon aromatic ring, a heteroaromatic ring, or a substituted heteroaromatic ring. n represents 0 or 1. $\pi^1$ and $\pi^2$ represent $\pi$-conjugated units that may be the same or different and are each a divalent hydrocarbon aromatic ring, a substituted divalent hydrocarbon aromatic ring, a divalent heteroaromatic ring, or a substituted divalent heteroaromatic ring. —NR$^3$R$^4$ is bound to the position of $\pi^1$ or $\pi^2$ at which electrons can be donated to the phosphole skeleton.

Advantageous Effects of Invention

The phosphole compound of the present invention has the characteristic of maintaining a high fluorescence quantum yield in a wide range of solvents from low-polarity to high-polarity solvents, as well as the characteristic in which the fluorescence wavelength shifts to the longer wavelength side as the polarity of the solvent increases. Because of these characteristics, the phosphole compound of the present invention is expected to be used, for example, for quantitatively determining the polarity in the environment therearound by using the absorption wavelength and fluorescence wavelength thereof, or used as a new fluorescent probe dye or a highly efficient luminescent material in organic electronic devices. In particular, the phosphole compound of formula (2) exhibits very high resistance to light. Fluorescent probe dyes are observed through a high-resolution laser microscope in some cases. The phosphole compound of formula (2) can keep the degree of color high even by being irradiated with strong laser light for a long time for such microscope observation because this compound is highly resistant to light.

DESCRIPTION OF EMBODIMENTS

Figure 1:
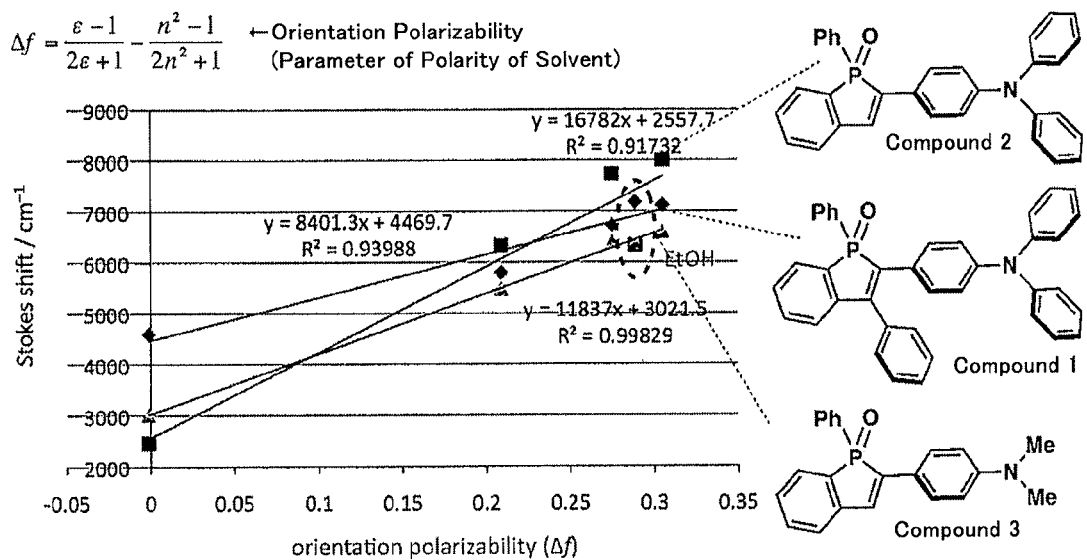
FIG. 1 is a graph showing the relationships of Compounds 1 to 3 between orientation polarizability Δf and Stokes shift.

The phosphole compound of the present invention is represented by the above-described formula (1) or formula (2). The phosphole compound of the present invention has a phosphole skeleton having a high ability to accept electrons and an amino group-containing π-conjugated unit having a high ability to donate electrons.

R$^1$ represents an alkyl group, a substituted alkyl group, an aryl group, a substituted aryl group, an alkoxy group, a hydroxy group, an amino group, or a substituted amino group.

The alkyl group may be, for example, a linear, branched or cyclic alkyl group having a carbon number of 1 to 20. Examples thereof include methyl, ethyl, n-propyl, isopropyl, n-butyl, isobutyl, sec-butyl, tert-butyl, n-amyl, isoamyl, sec-amyl, tert-amyl, cyclopropyl, cyclobutyl, cyclopentyl, and cyclohexyl. The substituted alkyl group may be, for example, a linear, branched or cyclic alkyl group having a carbon number of 1 to 20 whose one or more hydrogen atoms are substituted with, for example, a halogen atom, a cyano group, a nitro group, an amino group, a mono or dialkylamino group, or a mono or diarylamino group. The halogen atom may be fluorine, chlorine, bromine, or iodine.

Examples of the aryl group include phenyl, tolyl, xylyl, trimethylphenyl, naphthyl, and anthracenyl and, in addition, thienyl, furyl, and pyridyl. The substituted aryl group may be, for example, an aryl group whose one or more hydrogen atoms are substituted with, for example, a halogen atom, an alkyl group, an alkenyl group, an alkynyl group, an alkoxy group, a carbonyl group, a cyano group, or a nitro group. Examples of the alkyl group are the same as cited above. Examples of the alkenyl group include ethenyl, propenyl, butenyl, and isobutenyl.

Examples of the alkynyl group include ethynyl, propynyl, and butynyl. Alkoxy groups are represented by —OR, and the R of the alkoxy group used herein include not only alkyl groups, but also groups having an ether linkage defined by alkyl chains with an oxygen atom therebetween. More specifically, examples of the alkoxy group include methoxy, ethoxy, n-propoxy, isopropoxy, n-butoxy, isobutoxy, sec-butoxy, and tert-butoxy and, in addition, —O((CH$_2$)$_p$O)$_q$CH$_3$ (p represents an integer of 1 to 3, and q represents an integer of 1 to 10).

The carbonyl group may be, for example, a formyl group or an acyl group (such as methylcarbonyl or ethylcarbonyl).

The amino group is represented by —NH$_2$. The substituted amino group is an amino group whose one or more hydrogen atoms are substituted with, for example, an alkyl group, a substituted alkyl group, an aryl group, or a substituted aryl group. Examples of the alkyl, the substituted alkyl, the aryl, and the substituted aryl group are the same as cited above.

R$^2$ represents a hydrogen atom, an alkyl group, a substituted alkyl group, an aryl group, a substituted aryl group, a carbonyl group, an imino group, a cyano group, or a fluorine atom. Examples of the alkyl, the substituted alkyl, the aryl, the substituted aryl, and the carbonyl group are the same as cited above. The imino group may be, for example, an alkylimino group, a substituted alkylimino group, an arylimino group, a substituted arylimino group, or a sulfonylimino group. The sulfonylimino group is an imino group having a nitrogen atom to which —SO$_2$R is bound, and the R thereof may be, for example, an alkyl group, a substituted alkyl group, an aryl group, or a substituted aryl group. Examples of the alkyl, the substituted alkyl and other groups of the imino group are the same as cited above.

R$^3$ and R$^4$ may be the same or different and are each a hydrogen atom, an alkyl group, a substituted alkyl group, an aryl group, or a substituted aryl group. Examples of the alkyl, the substituted alkyl, the aryl, and the substituted aryl group are the same as cited above.

R$^5$ and R$^6$ may be the same or different and are each a hydrogen atom, an alkyl group, a substituted alkyl group, an aryl group, or a substituted aryl group. Examples of the alkyl, the substituted alkyl, the aryl, and the substituted aryl group are the same as cited above.

Ar represents a hydrocarbon aromatic ring, a substituted hydrocarbon aromatic ring, a heteroaromatic ring, or a substituted heteroaromatic ring.

The hydrocarbon aromatic ring may be, for example, a benzene ring, a naphthalene ring, an anthracene ring, or a phenanthrene ring. The substituted hydrocarbon aromatic ring may be a hydrocarbon aromatic ring whose one or more hydrogen atoms are substituted with, for example, a halogen atom, an alkyl group, a perfluoroalkyl group, an alkenyl group, an alkynyl group, an alkoxy group, a carbonyl group, a cyano group, or a nitro group. Examples of the perfluoroalkyl group include trifluoromethyl and pentafluoroethyl. Examples of other substituents are the same as cited above.

Examples of the heteroaromatic ring include a thiophene ring, a thiazole ring, a pyrrole ring, an imidazole ring, a furan ring, an oxazole ring, and a pyridine ring and, in addition, condensed rings of a heteroaromatic ring with a hydrocarbon aromatic ring and condensed rings of heteroaromatic rings. The substituted heteroaromatic ring may be a heteroaromatic ring whose one or more hydrogen atoms are substituted with, for example, a halogen atom, an alkyl group, a perfluoroalkyl group, an alkenyl group, an alkynyl group, an alkoxy group, a carbonyl group, a cyano group, or a nitro group. Examples of these substituents are the same as cited above.

$\pi^1$ and $\pi^2$ represent π-conjugated units that may be the same or different. The π-conjugated units in formula (1) are each a divalent alkenyl group, a substituted divalent alkenyl group, a divalent alkynyl group, a substituted divalent alkynyl group, a divalent hydrocarbon aromatic ring, a substituted divalent hydrocarbon aromatic ring, a divalent heteroaromatic ring, or a substituted divalent heteroaromatic ring, and the π-conjugated units in formula (2) are each a divalent hydrocarbon aromatic ring, a substituted divalent hydrocarbon aromatic ring, a divalent heteroaromatic ring, or a substituted divalent heteroaromatic ring.

Examples of the alkenyl group include ethenyl, propenyl, butenyl, and isobutenyl. The substituted alkenyl group may be an alkenyl group whose one or more hydrogen atoms are substituted with a halogen atom.

Examples of the alkynyl group include ethynyl, propynyl, and butynyl. The substituted alkynyl group may be an alkynyl group whose one or more hydrogen atoms are substituted with a halogen atom.

The examples of the hydrocarbon aromatic ring, the substituted hydrocarbon aromatic ring, the heteroaromatic ring, and the substituted heteroaromatic ring are the same as cited above.

—$NR^3R^4$ is bound to the position of $\pi^1$ or $\pi^2$ at which electrons can be donated to the phosphole skeleton. In the case of formula (1), for example, when n is zero and $\pi^1$ represents a benzene ring, —$NR^3R^4$ is preferably located at the para-position of the benzene ring. When n is 1 and $\pi^1$ and $\pi^2$ are benzene rings, preferably, the benzene ring represented by $\pi^2$ is located at the para-position of the benzene ring represented by $\pi^1$, and —$NR^3R^4$ is located at the para-position of the benzene ring represented by $\pi^2$.

Preferably, $R^1$ is an aryl group or a substituted aryl group. Preferably, $R^2$ is a hydrogen atom, an aryl group, or a substituted aryl group. $R^3$ and $R^4$ may be the same or different and are each preferably an alkyl group, a substituted alkyl group, an aryl group, or a substituted aryl group. $R^5$ and $R^6$ may be the same or different and are each preferably an alkyl group, a substituted alkyl group, an aryl group, or a substituted aryl group. Preferably, Ar is a benzene ring or a naphthalene ring. In the case of formula (1), it is preferable that n be zero, that $\pi_1$ represent a benzene ring, and that —$NR^3R^4$ be located at the para-position of the benzene ring $\pi^1$. In the case of formula (2), it is preferable that n be zero, that it, represent a benzene ring, and that —$NR^3R^4$ be located at the 5- or the 6-position of the indene ring. In these cases, $R^3$ and $R^4$ are each an alkyl group or a substituted alkyl group and may be bound to the benzene ring $\pi^1$ to form an alkylene chain or a substituted alkylene chain. In particular, the phosphole compound of the present invention is preferably represented by the following formula (1') or (2').

[Chem. 3]

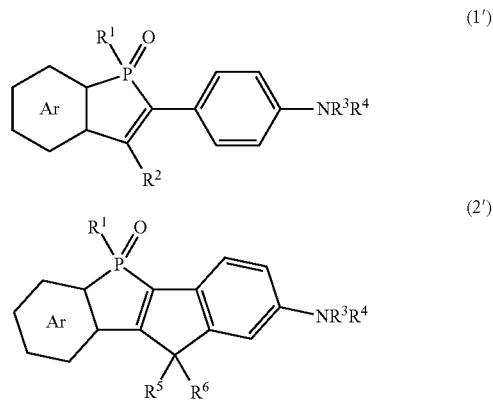

The phosphole compound of the present invention can be used in a fluorescent dye. For example, if a fluorescent dye containing the phosphole compound is added to an environment, it can be known what polarity the environment around the fluorescent dye has changed to by measuring the Stokes shift of the environment. Also, if viable cells are stained with the fluorescent dye, the polarity of the environment around the cells can be known by examining the luminescent color of the stained cells. Thus, the fluorescent dye enables imaging of intracellular environment. Furthermore, the fluorescent dye can be used in organic electronic devices as a highly efficient luminescent material.

EXAMPLES

1. General Operation $^1$H, $^{13}$C and $^{31}$P NMR spectra were recorded with a JEOL A-400 spectrometer (resonance frequencies $^1$H: 400 MHz, $^{13}$C: 100 MHz, $^{31}$P: 162 MHz). The chemical shifts in $^1$H NMR spectra are determined using the signals for residual proton of the deuterated solvents $CDCl_3$ (7.26 ppm) and $CD_2Cl_2$ (5.30 ppm) as an internal standard. The chemical shifts in $^{13}$C NMR spectra are determined using the solvent signals of $CDCl_3$ (77.16 ppm) and $CD_2Cl_2$ (53.84 ppm) as an internal standard. The chemical shifts in $^{31}$P NMR spectra are reported using $H_3PO_4$ (0.00 ppm) as an external standard. Thin layer chromatography (TLC) was performed on glass plates coated with silica gel $60F_{254}$ (Merck). Column chromatography was performed using PSQ100B (Fuji Silysia Chemicals). Recycling preparative HPLC was performed using LC-918 (Japan Analytical Industry) equipped with silica gel column (Wakosil-II 5-Prep, Wako). Recycling preparative gel permeation chromatography (GPC) was performed using LC-918 (Japan Analytical Industry) equipped with polystyrene gel columns (JAIGEL 1H and 2H, Japan Analytical Industry) and $CHCl_3$ as an eluent. Anhydrous solvents were purchased from Kanto Chemicals and further purified by Organic Solvent Purification System (Glass Contour). Degassed solvents were each prepared by purging with an argon gas stream into a solvent for more than 20 minutes. Reaction was conducted under an argon atmosphere unless otherwise specified.

2. Synthesis (1) Synthesis of 2-[4-(N,N-diphenylamino)phenyl]-1,3-diphenylbenzo[b]phosphole-P-oxide (Compound 1)

Compound 1 was synthesized by the following scheme.

[Chem. 4]

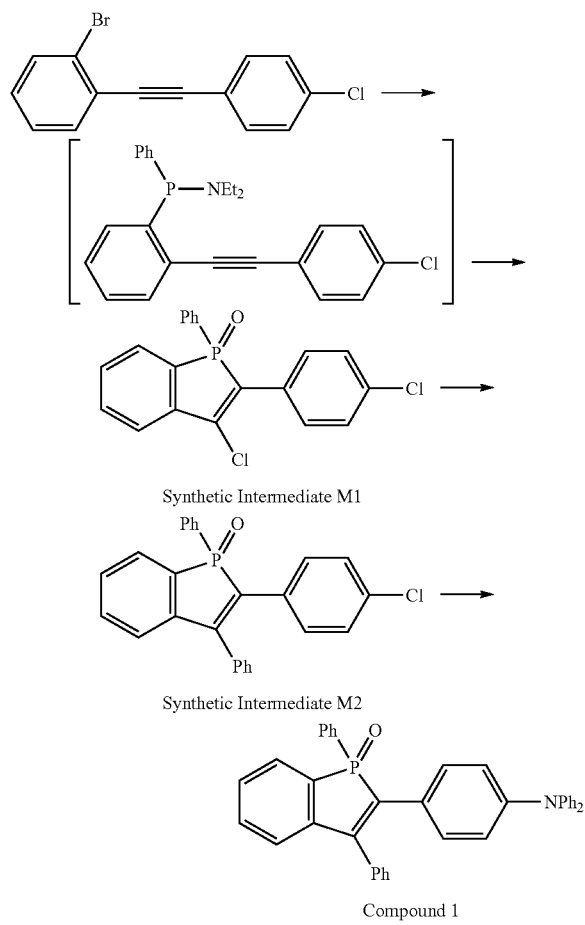

Synthetic Intermediate M1

Synthetic Intermediate M2

Compound 1

In dehydrated THF (3 mL) was dissolved 1-bromo-2-[(4-chlorophenyl)ethynyl]benzene (0.508 g, 1.74 mmol) that is a known compound described in literature (Org. Lett. 2012, vol. 14, No. 23, pp. 6032-6035). A solution of t-BuLi in pentane (1.65 M, 2.10 mL, 3.48 mmol) was added dropwise at −78° C. over 3 minutes. The mixture was stirred for 45 minutes PhP(NEt$_2$)Cl (0.350 mL, 392 mg, 1.75 mmol) was added and the resulting mixture was stirred for 1.5 hours. Then, PBr$_3$ (0.164 mL, 471 mg, 1.74 mmol) was added and the reaction mixture was warmed to room temperature and stirred for 19 hours. Subsequently, 30% H$_2$O$_2$ solution (1 mL) was added at 0° C., followed by stirring at room temperature for one hour. After adding saturated Na$_2$SO$_3$ aqueous solution into the reaction mixture, the solvent was concentrated under reduced pressure, and extraction was performed with chloroform. The combined organic layer was washed with brine, and dehydrated over anhydrous sodium sulfate. The sodium sulfate was removed by filtration, and the filtrate was concentrated under reduced pressure to yield a crude product. The crude product was purified through a silica gel column chromatography (CHCl$_3$/AcOEt 20:1, R$_f$ 0.28) to yield 358 mg (0.861 mmol, yield: 49%) of 3-bromo-2-(4-chlorophenyl)-1-phenylbenzo[b]phosphole-P-oxide (synthetic intermediate M1) as colorless solids. The spectral data of synthetic intermediate M1 are as follows:

$^1$H NMR (400 MHz, CDCl$_3$): δ 7.74 (dd, J$_{CP}$=8.0 Hz, 3.2 Hz, 1H), 7.68-7.60 (m, 6H), 7.52-7.45 (m, 2H), 7.39 (dt, J$_{CP}$=7.6 Hz, 3.2 Hz, 2H), 7.33 (d, J=8.4 Hz, 2H). $^{13}$C[$^1$H] NMR (100 MHz, CD$_2$Cl$_2$): δ 141.91 (d, J$_{CP}$=22.2 Hz, C), 136.16 (d, J$_{CP}$=87.3 Hz, C), 135.31 (C), 133.94 (d, J$_{CP}$=1.6 Hz, CH), 133.28 (d, J$_{CP}$=36.2 Hz, C), 133.08 (d, J$_{CP}$=2.4 Hz, CH), 131.61 (d, J$_{CP}$=105.4 Hz, C), 131.29 (d, J$_{CP}$=10.7 Hz, CH), 131.23 (d, J$_{CP}$=8.3 Hz, C), 130.83 (d, J$_{CP}$=11.5 Hz, CH), 130.32 (d, J$_{CP}$=5.0 Hz, CH), 129.42 (d, J$_{CP}$=20.6 Hz, CH), 129.24 (s, CH), 129.18 (d, J$_{CP}$=103.2 Hz, C), 128.82 (d, J$_{CP}$=9.1 Hz, CH), 125.41 (d, J$_{CP}$=9.9 Hz, CH). $^{31}$P [$^1$H] NMR (161.70 MHz, CD$_2$Cl$_2$): δ 34.20. HRMS (APCI): m/z calcd. for C$_{20}$H$_{14}$$^{79}$BrClOP: 414.9654 ([M+H]$^+$); found. 414.9670.

Degassed toluene (8.5 mL) and degassed water (1.7 mL) were added into the mixture of synthetic intermediate M1 (358 mg, 0.861 mmol), phenylboronic acid (115 mg, 0.947 mmol), Pd$_2$(dba)$_3$.CHCl$_3$ (22 mg, 0.022 mmol), S-Phos (18 mg, 0.043 mmol), and K$_3$PO$_4$ (270 mg, 1.27 mmol). The resulting mixture was heated at 80° C. for 12 hours. After extraction with chloroform, the combined organic layer was washed with brine and dehydrated over anhydrous sodium sulfate. The sodium sulfate was removed by filtration, and the filtrate was concentrated under reduced pressure to give a crude product. The crude product was purified through a silica gel column chromatography (CHCl$_3$/AcOEt=10:1, R$_f$=0.40) to give 338 mg (0.819 mmol, yield: 95%) of synthetic intermediate M2 as colorless solids. The spectral data of synthetic intermediate M2 are as follows:

$^1$H NMR (400 MHz, CD$_2$Cl$_2$): δ 7.73-7.63 (m, 6H), 7.51-7.37 (m, 8H), 7.33-7.31 (m, 2H), 7.22 (dd, J=8.0, 3.2 Hz, 1H), 7.17 (d, J=8.4 Hz, 2H), 7.07 (d, J=8.4 Hz, 2H). $^{13}$C[$^1$H] NMR (100 MHz, CD$_2$Cl$_2$): δ 150.94 (d, J$_{CP}$=20.6 Hz, C), 143.89 (d, J$_{CP}$=26.4 Hz, C), 134.33 (d, J$_{CP}$=14.0 Hz, C), 134.07 (s, C), 133.59 (d, J$_{CP}$=94.7 Hz, C), 133.40 (d, J$_{CP}$=1.6 Hz, CH), 132.66 (d, J$_{CP}$=2.4 Hz, CH), 132.60 (d, J$_{CP}$=103.7 Hz, C), 132.03 (d, J$_{CP}$=9.9 Hz, C), 131.27 (d, J$_{CP}$=10.7 Hz, CH), 130.71 (d, J$_{CP}$=5.8 Hz, CH), 130.40 (d, J$_{CP}$=98.8 Hz, C), 129.74 (d, J$_{CP}$=10.7 Hz, CH), 129.48 (s, CH), 129.39 (s, CH), 129.33 (d, J$_{CP}$=13.2 Hz, CH), 129.28 (s, CH), 129.18 (d, J$_{CP}$=9.1 Hz, CH), 128.87 (s, CH), 124.66 (d, J$_{CP}$=10.7 Hz, CH). $^{31}$P [$^1$H] NMR (38.16 MHz, CD$_2$Cl$_2$): δ 38.16. HRMS (APCI): m/z calcd. for C$_{26}$H$_{19}$ClOP: 413.0857 ([M+H]$^+$); found. 413.0854.

Dehydrated toluene (1 mL) was added to the mixture of synthetic intermediate M2 (74.7 mg, 0.181 mmol), diphenylamine (31.5 mg, 0.186 mmol), Pd(dba)$_2$ (2.3 mg, 0.0040 mmol), Q-Phos (5.0 mg, 0.0069 mmol), and t-BuONa (18.0 mg, 0.187 mmol), and the resulting mixture was stirred at 80° C. for 24 hours. Subsequently, 1N NH$_4$Cl aqueous solution was added, and extraction was performed with toluene. The combined organic layer was washed with brine and dehydrated over anhydrous sodium sulfate. The sodium sulfate was removed by filtration, and the filtrate was concentrated under reduced pressure to give a crude product.

The crude product was subjected to silica gel column chromatography (CHCl$_3$/AcOEt=20:1, R$_f$=0.35) and then further purified by HPLC to give 43.4 mg (0.0795 mmol, yield: 44%) of compound 1 as yellow solids. The spectral data of compound 1 are as follows:

$^1$H NMR (400 MHz, CD$_2$Cl$_2$): δ 7.76 (ddd, J=12.0, 7.8, 1.2 Hz, 2H), 7.59 (t, J=8.8 Hz, 1H), 7.51-7.30 (m, 10H), 7.21-7.17 (m, 4H), 7.10 (dd, J=7.6, 2.8 Hz, 1H), 7.05-6.96 (m, 8H), 6.67 (d, J=8.8 Hz, 2H). $^{13}$C[$^1$H] NMR (100 MHz, CD$_2$Cl$_2$): δ 148.38 (d, J$_{CP}$=21.4 Hz, C), 147.27 (s, C), 147.48 (s, C), 144.61 (d, J$_{CP}$=27.2 Hz, C), 135.43 (d, J$_{CP}$=14.8 Hz, C), 134.05 (d, J$_{CP}$=94.6 Hz, C), 133.29 (s, CH), 132.59 (d, J$_{CP}$=104.6 Hz, C), 132.47 (d, J$_{CP}$=2.5 Hz, CH), 131.50 (d, J$_{CP}$=98.0 Hz, C), 131.29 (d, J$_{CP}$=10.7 Hz, CH), 130.24 (d, J$_{CP}$=5.7 Hz, CH), 129.71 (s, CH), 129.52 (s, CH), 129.42 (s, CH), 129.31 (d, J$_{CP}$=12.3 Hz, CH), 129.14 (d, J$_{CP}$=10.7 Hz, CH), 128.98 (s, CH), 128.88 (d, J$_{CP}$=9.8 Hz, CH), 126.31 (d, J$_{CP}$=10.7 Hz, C), 125.57 (s, CH), 124.13 (d, J$_{CP}$=10.7 Hz, CH), 124.02 (s, CH), 121.71 (s, CH). $^{31}$P [$^1$H] NMR (161.70 MHz, CD$_2$Cl$_2$): δ 38.29. HRMS (APCI): m/z calcd. for C$_{38}$H$_{29}$NOP: 546.1981 ([M+H]$^+$); found. 546.1990.

(2) Synthesis of 2-[4-(N,N-diphenylamino)phenyl]-1-phenylbenzo[b]phosphole-P-oxide (Compound 2)

Compound 2 was synthesized by the following scheme.

[Chem. 5]

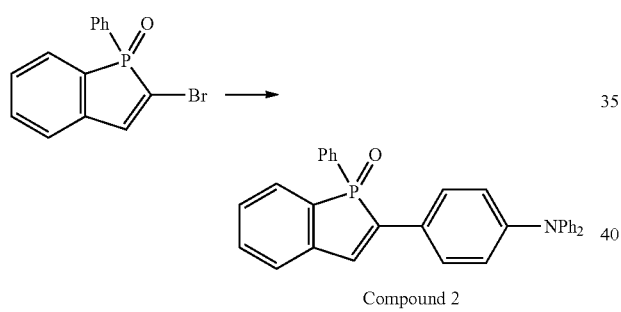

Compound 2

Degassed toluene (4 mL) and degassed water (1 mL) were added into the mixture of 2-bromo-1-phenylbenzo[b]phosphole-P-oxide (60.3 mg, 0.198 mmol) that is a known compound described in literature (Chem. Eur. 2012, vol. 18, pp. 15972-15983), diphenylaminophenylboronic acid (88.6 mg, 0.306 mmol), Pd$_2$(dba)$_3$.CHCl$_3$ (5.4 mg, 0.0052 mmol), S-Phos (4.3 mg, 0.011 mmol), and K$_3$PO$_4$ (62.9 mg, 0.296 mmol), and the resulting mixture was stirred at 80° C. for 1.5 hours. Then, 1N NH$_4$Cl aqueous solution was added, and extraction was performed with toluene. The combined organic layer was washed with brine and dehydrated with anhydrous sodium sulfate. The sodium sulfate was removed by filtration, and the filtrate was concentrated under reduced pressure to give a crude product. The crude product was subjected to silica gel column chromatography (CHCl$_3$/Et$_3$N=20:1, R$_f$=0.45) and then further purified by HPLC and GPC to afford 53.3 mg (114 mmol, yield: 58%) of compound 2 as yellow solids. The spectral data of compound 2 are as follows:

$^1$H NMR (400 MHz, CD$_2$Cl$_2$): δ 7.71 (ddd, J=12.4, 7.2, 1.2 Hz, 2H), 7.53-7.44 (m, 6H), 7.42-7.37 (m, 3H), 7.31-7.22 (m, 5H), 7.06-7.02 (m, 6H), 6.93 (d, J=8.4 Hz, 2H). $^{13}$C[$^1$H] NMR (100 MHz, CD$_2$Cl$_2$): δ 148.92 (s, C), 147.49 (s, C), 142.57 (d, J$_{CP}$=28.0 Hz, C), 138.62 (d, J$_{CP}$=93.0 Hz, C), 134.36 (d, J$_{CP}$=19.8 Hz, CH), 133.57 (d, J$_{CP}$=1.7 Hz, CH), 133.15 (d, J$_{CP}$=107.8 Hz, C), 132.52 (d, J$_{CP}$=2.4 Hz, CH), 131.14 (d, J$_{CP}$=96.4 Hz, C), 131.09 (d, J$_{CP}$=10.7 Hz, CH), 129.77 (s, CH), 129.29 (d, J$_{CP}$=11.5 Hz, CH), 128.96 (d, J$_{CP}$=9.9 Hz, CH), 127.79 (d, J$_{CP}$=6.6 Hz, CH), 126.20 (d, J$_{CP}$=10.7 Hz, C), 125.53 (s, CH), 124.76 (d, J$_{CP}$=9.1 Hz, CH), 124.09 (s, CH), 122.62 (s, CH). $^{31}$P [$^1$H] NMR (161.70 MHz, CD$_2$Cl$_2$): δ 38.44. HRMS (APCI): m/z calcd. for C$_{32}$H$_{25}$NOP: 470.1674 ([M+H]$^+$); found. 470.1681.

(3) Synthesis of 2-[4-(N,N-dimethylamino)phenyl]-1-phenylbenzo[b]phosphole-P-oxide (Compound 3)

Compound 3 was synthesized by the following scheme.

[Chem. 6]

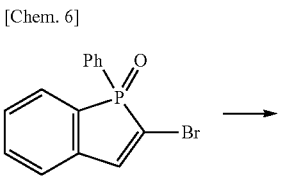

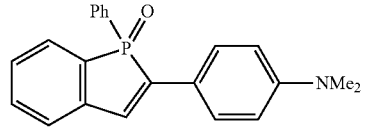 [SMILES: CN(C)c1ccc(C2=Cc3ccccc3P2(=O)c2ccccc2)cc1]

Compound 3

Degassed toluene (4 mL) and degassed water (1 mL) were added into the mixture of 2-bromo-1-phenylbenzo[b]phosphole-P-oxide (61.5 mg, 0.202 mmol) that is a known compound described in literature (Chem. Eur. J. 2012, vol. 18, p. 15972), dimethylaminophenylboronic acid (51.6 mg, 0.313 mmol), Pd$_2$(dba)$_3$.CHCl$_3$ (6.1 mg, 0.0059 mmol), S-Phos (4.7 mg, 0.011 mmol), and K$_3$PO$_4$ (63.7 mg, 0.300 mmol), and the resulting mixture was stirred at 80° C. for one hour. Then, distilled water was added, and extraction was performed with toluene. The combined organic layer was washed with brine and dehydrated with anhydrous sodium sulfate. The sodium sulfate was removed by filtration, and the filtrate was concentrated under reduced pressure to give a crude product. The crude product was subjected to silica gel column chromatography (CHCl$_3$/Et$_3$N=20:1, R$_f$=0.50) and then further purified by HPLC. The purified product was recrystallized twice from chloroform and hexane to a 6.6 mg (0.0191 mmol, yield: 9.5%) of compound 3 as yellow solids. The spectral data of compound 3 are as follows:

$^1$H NMR (400 MHz, CD$_2$Cl$_2$): δ 7.71 (dd, J=12.4, 7.2 Hz, 2H), 7.60 (d, J=8.4 Hz, 2H), 7.53-7.45 (m, 4H), 7.40-7.35 (m, 3H), 7.26 (td, J=7.2, 4.0 Hz, 1H), 6.77 (s, br, 2H), 2.95 (s, 6H). $^{31}$P[$^1$H] NMR (161.70 MHz, CD$_2$Cl$_2$): δ 38.84. HRMS (APCI): m/z calcd. for C$_{22}$H$_{21}$NOP: 346.1361 ([M+H]$^+$); found. 346.1371.

(4) Synthesis of 2-[4-(N,N-dimethylamino)phenyl]-1,3-diphenylbenzo[b]phosphole-P-oxide (Compound 4)

Compound 4 was synthesized by the following scheme.

[Chem. 7]

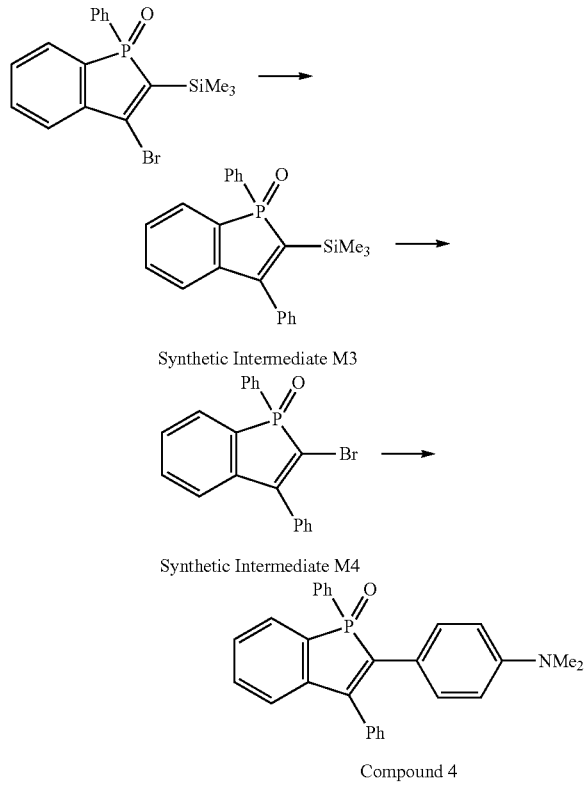

Degassed toluene (10 mL) and degassed water (2.5 mL) were added into the mixture of 3-bromo-1-phenyl-2-trimethylsilylbenzo[b]phosphole-P-oxide (0.490 g, 1.30 mmol) that is a known compound described in literature (Chem. Asian J. 2009, vol. 4, p. 1729), phenylboronic acid (0.174 g, 1.43 mmol), Pd(PPh$_3$)$_4$ (0.149 g, 0.129 mmol), and K$_3$PO$_4$ (0.408 g, 1.92 mmol), and the resulting mixture was heated at 80° C. for 25 hours. Then, distilled water was added, and extraction was performed with toluene. The combined organic layer was washed with brine and dehydrated with anhydrous sodium sulfate. The sodium sulfate was removed by filtration, and the filtrate was concentrated under reduced pressure to give a crude product. The crude product was purified by silica gel column chromatography (CHCl$_3$/AcOEt=10:1, R$_f$=0.30) to yield 0.413 g (1.10 mmol, yield: 85%) of 1,3-diphenyl-2-trimethylsilylbenzo[b]phosphole [P] oxide (synthetic intermediate M3) as white solids.

Subsequently, acetonitrile (10 mL) was added into the mixture of synthetic intermediate M3 (0.413 g, 1.10 mmol) and NBS (0.217 g, 1.22 mmol) in the air, and the mixture was heated to reflux for 8 hours. Then, distilled water was added, and extraction was performed with chloroform. The combined organic layer was washed with brine and then dehydrated with anhydrous sodium sulfate. The sodium sulfate was removed by filtration, and the filtrate was concentrated under reduced pressure to yield a crude product. The crude product was purified by silica gel column chromatography (CHCl$_3$/AcOEt=10:1, R$_f$=0.40) to yield 0.393 g (1.03 mmol, yield: 94%) of 2-bromo-1,3-diphenylbenzo[b]phosphole-P-oxide (synthetic intermediate M4) as white solids.

Degassed toluene (4 mL) and degassed water (1 mL) were added into the mixture of synthetic intermediate M4 (0.194 g, 0.509 mmol), dimethylaminophenylboronic acid (0.102 g, 0.619 mmol), Pd$_2$(dba)$_3$·CHCl$_3$ (15.6 mg, 0.0151 mmol), S-Phos (12.3 mg, 0.0300 mmol), and K$_3$PO$_4$ (0.159 g, 0.750 mmol). The resulting mixture was stirred at 80° C. for 12 hours. Then, distilled water was added, the toluene was removed, and extraction was performed with chloroform. The organic phase collected was washed with brine and dehydrated with anhydrous sodium sulfate. The sodium sulfate was removed by filtration, and the filtrate was concentrated under reduced pressure to yield a crude product containing compound 4. The crude product was subjected to silica gel column chromatography (CHCl$_3$/AcOEt=10:1, R$_f$=0.25) and then further purified by HPLC and GPC to yield compound 4 as yellow solids.

$^1$H NMR (400 MHz, CD$_2$Cl$_2$): δ 7.75 (ddd, J=12.4, 7.6, 1.2 Hz, 2H), 7.58 (t, J=8.8 Hz, 1H), 7.49-7.35 (m, 9H), 7.28 (td, J=7.2, 4 Hz, 1H), 7.14 (d, J=8.4 Hz, 2H), 7.07 (dd, J=7.6, 2.8 Hz, 1H), 6.41 (s, br, 2H), 2.83 (s, 6H). $^{31}$P[$^1$H] NMR (161.70 MHz, CD$_2$Cl$_2$): δ 38.67. HRMS (APCI): m/z calcd. for C$_{28}$H$_{25}$NOP: 422.1674 ([M+H]$^+$); found. 422.1691.

(5) Synthesis of 2-[(4-(N,N-dimethylamino)phenyl)-3-[4-(methyltriethyleneglycoxy)phenyl]-1-phenyl-benzo[b]phosphole-P-oxide (Compound 5)

Compound 5 was synthesized by the following scheme.

[Chem. 8]

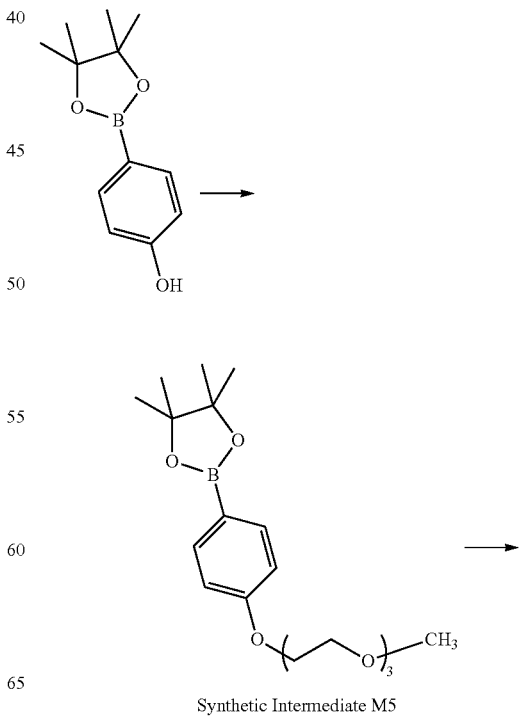

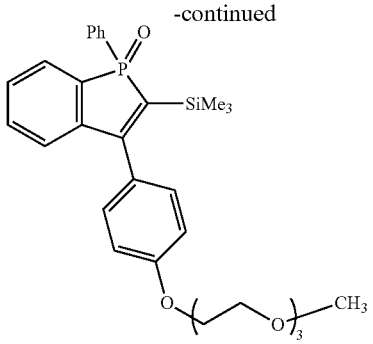

Synthetic Intermediate M6

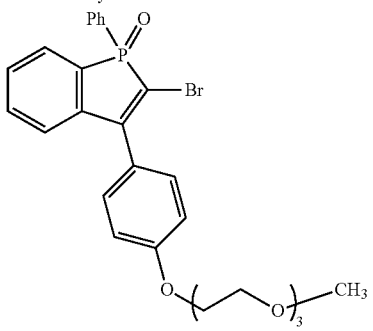

Synthetic Intermediate M7

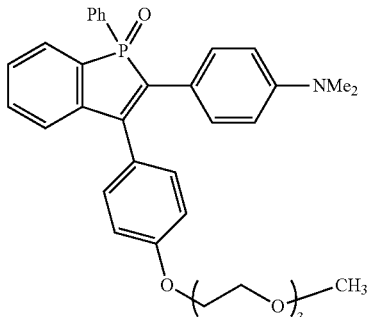

Compound 5

Dehydrated DMF (11 mL) was added to the mixture of (4-hydroxyphenyl)boronic acid pinacol ester (produced by Sigam-Aldrich, 1.68 g, 7.61 mmol), triethylene glycol methyl ether tosylate (2.42 g, 7.61 mmol), and $K_2CO_3$ (1.05 g, 7.61 mmol), and the resulting mixture was stirred at 80° C. for 16 hours. Then, chloroform as added, followed by filtration. The filtrate was washed with water, and dehydrated with anhydrous sodium sulfate. The sodium sulfate was removed by filtration, and the filtrate was concentrated under reduced pressure to yield a crude product. The crude product was purified by silica gel column chromatography (hexane/AcOEt=1:1, $R_f$=0.35) to yield 2.49 g (7.12 mmol, yield: 94%) of 4-(methyltriethyleneglycoxy)phenylboronic acid pinacol ester (synthetic intermediate M5) as pale yellow liquid.

Degassed toluene (24 mL) and degassed water (6 mL) were added into the mixture of 3-bromo-1-phenyl-2-trimethylsilylbenzo[b]phosphole-P-oxide (1.11 g, 3.00 mmol) that is a known compound described in literature (Chem. Asian J. 2009, vol. 4, p. 1729), synthetic intermediate M5 (1.32 g, 3.60 mmol), $Pd_2(dba)_3 \cdot CHCl_3$ (103.5 mg, 0.100 mmol), S-Phos (49.9 mg, 0.122 mmol), and $K_3PO_4$ (1.91 g, 9.00 mmol), and the resulting mixture was stirred at 80° C. for 12.5 hours. Then, an aqueous solution of ammonium chloride was added, and extraction was performed with chloroform. The combined organic layer was washed with brine and dehydrated with anhydrous sodium sulfate. The sodium sulfate was removed by filtration, and the filtrate was concentrated under reduced pressure to yield a crude product. The resulting crude product was subjected to silica gel column chromatography ($CHCl_3$/AcOEt=5:1+0.5% $Et_3N$, $R_f$=0.25), and further purified by GPC and HPLC to yield 3-[4-(methyltriethyleneglycoxy)phenyl]-1-phenyl-2-trimethylsilylbenzo[b]phosphole-P-oxide (synthetic intermediate M6) as colorless liquid.

Acetonitrile (2.5 mL) was added into the mixture of synthetic intermediate M6 (0.116 g, 0.216 mmol) and NBS (40.9 mg, 0.230 mmol), and the resulting mixture was stirred at 80° C. for 5 hours under the air. An aqueous solution of sodium sulfite was added, and extraction was performed with ethyl acetate. The combined organic layer was washed with brine and dehydrated with anhydrous sodium sulfate. The sodium sulfate was removed by filtration, and the filtrate was concentrated under reduced pressure to yield a crude product. The crude product was purified by silica gel column chromatography (AcOEt, $R_f$=0.30) to yield 97.3 mg (0.179 mmol, yield: 83%) of 2-bromo-3-[4-(methyltriethylglycoxy)phenyl]-1-phenylbenzo[b]phosphole-P-oxide (synthetic intermediate M7) as colorless liquid.

Degassed toluene (2 mL) and degassed water (0.5 mL) were added into the mixture of synthetic intermediate M7 (51.0 mg, 93.9 μmol), dimethylaminophenylboronic acid (27.1 mg, 0.164 mmol), $Pd_2(dba)_3 \cdot CHCl_3$ (2.1 mg, 0.0020 mmol), S-Phos (1.8 mg, 0.0044 mmol), and $K_3PO_4$ (30.3 mg, 0.143 mmol). The resulting mixture was stirred at 80° C. for 2.5 hours. Then, distilled water was added, and extraction was performed with chloroform. The combined organic layer was washed with brine and dehydrated with anhydrous sodium sulfate. The sodium sulfate was removed by filtration, and the filtrate was concentrated under reduced pressure to yield a crude product. The crude product was purified by silica gel column chromatography (hexane/AcOEt 1:10+1% $Et_3N$, $R_f$=0.30) to yield compound 5 as yellow solids. The spectral data of compound 5 are as follows:

$^1$H NMR (400 MHz, $CD_2Cl_2$): δ 7.74 (dd, J=12.0, 7.6 Hz, 2H), 7.58 (t, J=8.6 Hz, 1H), 7.49-7.36 (m, 4H), 7.32-7.27 (m, 3H), 7.17-7.15 (m, 3H), 7.01 (d, J=8.4 Hz, 2H), 6.49 (s, br, 2H), 4.16 (t, J=4.4 Hz, 2H), 3.84 (t, J=4.4 Hz, 2H), 3.70-3.67 (m, 2H), 3.63-3.58 (m, 4H), 3.51-3.48 (m, 2H), 3.32 (s, 3H), 2.86 (s, 6H). $^{31}$P [$^1$H] NMR (161.70 MHz, $CD_2Cl_2$): δ 38.28. HRMS (APCI): m/z calcd. for $C_{35}H_{39}NO_5P$: 584.2566 ([M+H]$^+$); found. 584.2570.

(6) Synthesis of Compounds 6a to 6d

Compounds 6a to 6d were synthesized by the following scheme. Since compound 6a is identical with compound 2 although the synthetic protocol thereof is different from that of compound 2, the synthetic protocol of compound 6b will be described in detail below by way of representative example.

[Chem. 9]

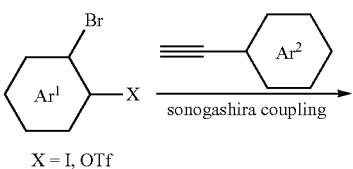

X = I, OTf

-continued

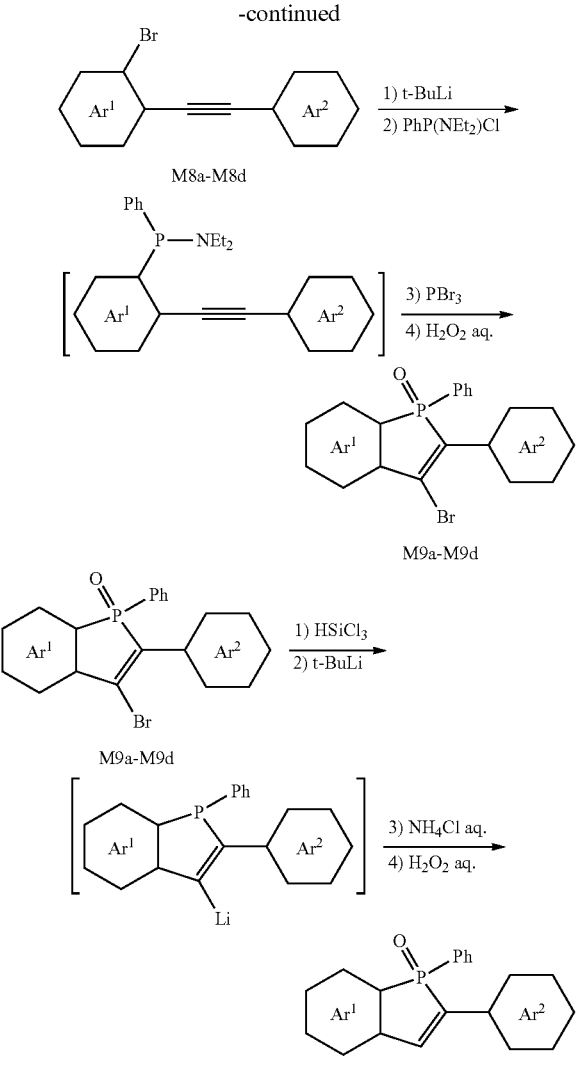

| | Ar¹ | Ar² |
|---|---|---|
| 6a | | |
| 6b | | |
| 6c | | |

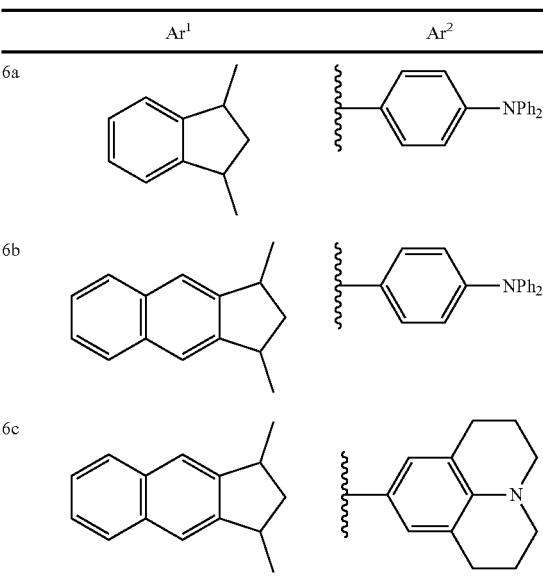

-continued

| | Ar¹ | Ar² |
|---|---|---|
| 6d | | |

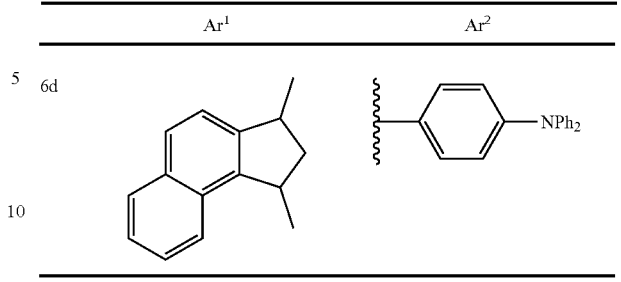

Compound 6b

The suspension of 2-bromo-3-iodonaphthalene (5 mmol), 4-(N,N-diphenylamino)phenylacetylene (5.25 mmol), Pd(PPh₃)₄ (0.10 mmol), CuI (0.10 mmol), toluene (10 mL), and i-Pr₂NH (5 mL) was stirred at room temperature for 20 hours. Then, inorganic salts were removed by filtration, and all the volatiles were evaporated under reduced pressure. The reaction product was subjected to silica gel chromatography (eluent: hexane/CH₂Cl₂=4/1), and then the resulting crude product was purified by recrystallization from MeOH to yield synthetic intermediate M8b as white powders in 96% yield.

A solution of t-BuLi (4.92 mmol) in n-pentane was added dropwise into the solution of synthetic intermediate M8b (2.4 mmol) in anhydrous THF (30 mL) at −78° C. Then, the mixture was slowly warmed up to −40° C. over 4 hours. After cooling the mixture to −78° C., PhP(NEt₂)Cl (2.40 mmol) was added, and the mixture was slowly warmed up to room temperature over 2 hours. The mixture was cooled to −78° C. again, and then, PBr₃ (2.40 mmol) was added. The resulting mixture was warmed up to room temperature. After being stirred at room temperature for 36 hours, the reaction mixture was oxidized with a H₂O₂ aqueous solution (2 mL, 30%) at 0° C. with stirring for one hour. The reaction was quenched at 0° C. with a Na₂SO₃ aqueous solution (50 mL, 10%), and then the mixture was subjected to extraction twice with EtOAc (100 mL). The combined organic layer was washed with H₂O (50 mL) and brine (50 mL) and then dehydrated with anhydrous Na₂SO₄, followed by filtration. The filtrate was concentrated under reduced pressure to yield solids. The resulting solids were purified by silica gel column chromatography (eluent was changed from CH₂Cl₂ to CH₂Cl₂/EtOAc=10/1) and recrystallized from MeOH to yield synthetic intermediate M9b as yellow powders in 47% yield.

Synthetic intermediate M9b (0.418 mmol) was suspended in anhydrous toluene (3 mL). HSiCl₃ (2.1 mmol) was added to the suspension in one portion at room temperature. After stirring for one hour, volatile substances were removed under reduced pressure. Then, toluene (2 mL) was added, and the resulting suspension was filtered through a plug of Celite in an argon atmosphere, followed by rinsing with toluene (4 mL). The filtrate was concentrated, and the resulting solid was dissolved in anhydrous THF (15 mL). A solution of t-BuLi in pentane (1.77 M, 0.70 mL, 1.24 mmol) was added to the resulting solution at −78° C. The mixture was stirred for one hour. The reaction was quenched with saturated NH₄Cl aqueous solution (1 mL), and the reaction mixture was allowed to stand to room temperature. Then, the mixture was oxidized with a H₂O₂ aqueous solution (1 mL, 30%) at 0° C. and stirred for one hour. The reaction was quenched at 0° C. with a Na₂SO₃ aqueous solution (20 mL, 10%), and then the mixture was subjected to extraction twice with EtOAc (50 mL). The combined organic layer was washed with H$_2$O (20 mL) and brine (20 mL) and then dehydrated with anhydrous Na$_2$SO$_4$, followed by filtration. The filtrate was concentrated under reduced pressure to yield a solid. The solid was purified by silica gel column chromatography (eluent was changed from CH$_2$Cl$_2$ to CH$_2$Cl$_2$/EtOAc=5/1) and recrystallized from MeOH (10 mL) to yield compound 6b as yellow powders in 84% yield. The spectral data of compound 6b are as follows:

R$_f$=0.30 (CH$_2$Cl$_2$/EtOAc=20/1); $^1$H NMR (400 MHz, CDCl$_3$): δ=8.06 (d, J=7.2 Hz, 1H), 7.84-7.73 (m, 5H), 7.65 (d, J=35.6 Hz, 1H), 7.57-7.38 (m, 7H), 7.27-7.23 (t, J=7.6 Hz, 4H), 7.09-7.03 (m, 6H), 6.97 (d, J=7.6 Hz, 2H); $^{13}$C NMR (100 MHz, CDCl$_3$): δ=148.18 (s, C), 146.77 (s, C), 138.66 (d, J=93.9 Hz, C), 137.88 (d, J=28.0 Hz, C), 135.56 (d, J=1.6 Hz, C), 134.86 (d, J=19.0 Hz, CH), 132.75 (d, J=11.5 Hz, C), 131.91 (d, J=2.5 Hz, CH), 130.84 (d, J=98.8 Hz, C), 130.72 (d, J=109.5 Hz, C), 130.65 (d, J=10.7 Hz, CH), 130.51 (d, J=9.9 Hz, CH), 129.16 (s, CH), 128.94 (s, CH), 128.66 (d, J=12.3 Hz, CH), 128.26 (s, CH), 127.46 (d, J=7.4 Hz, CH), 126.67 (s, CH), 125.78 (d, J=10.7 Hz, C), 124.79 (s, CH), 123.41 (s, CH), 123.00 (d, J=9.1 Hz, CH), 122.23 (s, CH), one of singlets corresponding to the carbon of CH could not been identified because they were overlapped with other signals; $^{31}$P NMR (162 MHz, CDCl$_3$): δ=38.24; HRMS (APCI): m/z calcd. for C$_{36}$H$_{27}$NOP: 520.1825 ([M+H]$^+$); found. 520.1831.

Compound 6c

Synthetic intermediate M8c was synthesized in accordance with the synthetic protocol of synthetic intermediate M8b, except that 4-(N,N-diphenylamino)phenylacetylene was replaced with 2-(2,3,6,7-tetrahydro-1H,5H-benzo[ij]quinolizin-9-yl)acetylene. Synthetic intermediate M9c was synthesized in accordance with the synthetic protocol of synthetic intermediate M9b, except that synthetic intermediate M8b was replaced with synthetic intermediate M8c. Compound 6c was synthesized in accordance with the synthesis of compound 6b, except that synthetic intermediate M9b was replaced with synthetic intermediate M9c. Compound 6c can be considered to be an example of the compound in which an alkylene chain (propylene chain) is formed by binding the alkyl group on N to the benzene ring of aniline. The spectral data of compound 6c are as follows:

R$_f$=0.21 (CH$_2$Cl$_2$/EtOAc=20/1); $^1$H NMR (400 MHz, CDCl$_3$): δ=8.07 (d, J=11.2 Hz, 1H), 7.89-7.78 (m, 4H), 7.66 (d, J=3.2 Hz, 1H), 7.57-7.32 (m, 8H), 3.20 (t, J=5.6 Hz, 4H), 2.82-2.67 (m, 4H), 1.98-1.93 (m, 4H); $^{13}$C NMR (100 MHz, CDCl$_3$): δ 143.70 (s, C), 139.76 (d, J=93.9 Hz, C), 138.90 (d, J=28.8 Hz, C), 136.11 (s, C), 132.84 (d, J=11.5 Hz, C), 131.90 (d, J=2.5 Hz, CH), 131.81 (d, J=98.8 Hz, C), 131.56 (d, J=18.9 Hz, CH), 131.41 (d, J=108.7 Hz, C), 131.01 (d, J=10.7 Hz, CH), 130.62 (d, J=9.8 Hz, CH), 129.31 (s, CH), 128.80 (d, J=11.5 Hz, CH), 128.33 (s, CH), 128.29 (s, CH), 126.42 (s, CH), 125.75 (d, J=7.5 Hz, CH), 121.82 (d, J=9.1 Hz, CH), 121.31 (s, C), 119.73 (d, J=10.7 Hz, C), 49.98 (s, CH), 27.80 (s, CH), 21.82 (s, CH); $^{31}$P NMR (162 MHz, CDCl$_3$): δ=38.51; HRMS (APCI): m/z calcd. for C$_{30}$H$_{27}$NOP: 448.1825 ([M+H]$^+$); found. 448.1831.

Compound 6d

Synthetic intermediate M8d was synthesized in accordance with the synthetic protocol of synthetic intermediate M8b, except that 2-bromo-3-iodonaphthalene was replaced with 1-bromonaphthalen-2-yl triflate. Synthetic intermediate M9d was synthesized in accordance with the synthetic protocol of synthetic intermediate M9b, except that synthetic intermediate M8b was replaced with synthetic intermediate M8d. Furthermore, compound 6d was synthesized in accordance with the synthetic protocol of compound 6b, except that synthetic intermediate M9b was replaced with synthetic intermediate M9d. The spectral data of compound 6d are as follows:

R$_f$=0.44 (CH$_2$Cl$_2$/EtOAc=20/1); $^1$H NMR (400 MHz, CD$_2$Cl$_2$): δ=8.04 (d, J=8.4 Hz, 1H), 7.97 (d, J=7.2 Hz, 1H), 7.86-7.81 (m, 3H), 7.65-7.56 (m, 4H), 7.50-7.37 (m, 5H), 7.30-7.26 (m, 4H), 7.10-7.06 (m, 6H), 6.98 (d, J=8.8 Hz, 2H); $^{13}$C NMR (100 MHz, CDCl$_3$): δ=148.57 (s, C), 147.20 (s, C), 141.74 (d, J=27.1 Hz, C), 139.42 (d, J=93.9 Hz, C), 134.20 (d, J=1.6 Hz, CH), 133.57 (d, J=8.3 Hz, 0), 133.36 (d, J=21.4 Hz, CH), 132.21 (d, J=2.4 Hz, CH), 132.01 (d, J=9.1 Hz, C), 130.80 (d, J=10.7 Hz, CH), 130.65 (d, J=95.5 Hz, C), 129.48 (s, CH), 129.15 (d, J=12.3 Hz, CH), 128.90 (s, CH), 128.50 (s, CH), 127.63 (d, J=6.5 Hz, CH), 127.54 (d, J=106.2 Hz, C), 126.47 (s, CH), 125.95 (d, J=11.6 Hz, C), 125.32 (d, J=4.1 Hz, CH), 125.22 (s, CH), 123.73 (s, CH), 122.58 (s, CH), 122.28 (d, J=10.7 Hz, CH); $^{31}$P NMR (162 MHz, CDCl$_3$): δ=40.52; HRMS (APCI): m/z calcd. for C$_{36}$H$_{27}$NOP: 520.1825 ([M+H]$^+$); found. 520.1822.

(7) Synthesis of Compounds 7a and 7b

Compounds 7a and 7b were synthesized by the following scheme.

[Chem. 10]

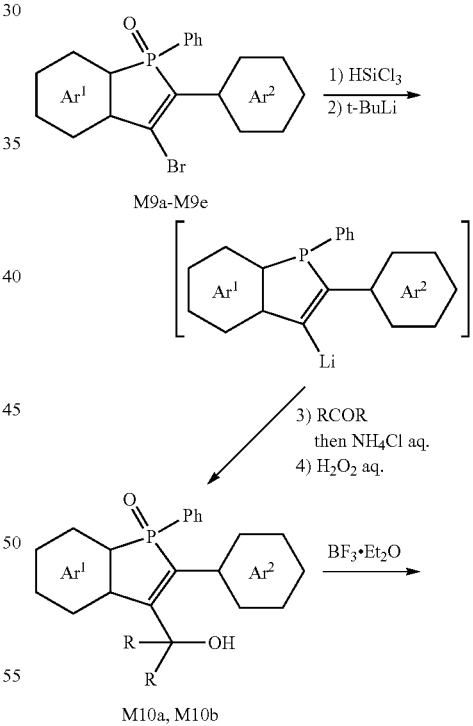

| | Ar¹ | Ar² | R |
|---|---|---|---|
| 7a | 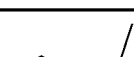 |  | Ph |
| 7b |  |  |  |

Compound 7a

Synthetic intermediate M9a (1.24 mmol) was suspended in anhydrous toluene (5 mL). HSiCl₃ (6.24 mmol) was added to the suspension in one portion at room temperature. After stirring for one hour, all the volatile substances were removed under reduced pressure. Then, toluene (5 mL) was added, and the resulting suspension was filtered through a plug of Celite under an argon atmosphere, followed by rinsing with toluene (5 mL). The filtrate was concentrated, and the resulting solid was dissolved in anhydrous THF (15 mL). A solution of t-BuLi in pentane (1.77 M, 1.47 mL, 2.60 mmol) was added to the resulting solution at −78° C. over 10 minutes. After stirring for one hour, benzophenone (2.74 mmol) was added in one portion, and the resulting mixture was slowly warmed up to room temperature over 6 hours. Then, the reaction was quenched at 0° C. with saturated NH₄Cl aqueous solution (2 mL). Subsequently, the reaction mixture was oxidized with a H₂O₂ aqueous solution (1 mL, 30%), followed by stirring at room temperature for one hour. The reaction was quenched with a Na₂SO₃ aqueous solution (20 mL, 10%), and then the mixture was subjected to extraction twice with EtOAc (50 mL). The combined organic layer was washed with H₂O (20 mL) and brine (20 mL) and then dehydrated with anhydrous Na₂SO₄, followed by filtration. The filtrate was concentrated under reduced pressure to yield a solid. The solid was purified by silica gel chromatography (eluent was changed from CH₂Cl₂ to CH₂Cl₂/EtOAc=2/1) to yield synthetic intermediate M10a in the form of pale yellow solid in 51% yield.

Subsequently, BF₃·OEt₂ (0.844 mmol) was added to the solution of synthetic intermediate M10a (0.422 mmol) in anhydrous CH₂Cl₂ (15 mL) at room temperature. After stirring for one hour, the reaction was quenched with EtOH (1 mL) and H₂O (30 mL), and the mixture was subjected to extraction twice with CH₂Cl₂ (50 mL). The combined organic layer was washed with H₂O (20 mL) and then dehydrated with anhydrous Na₂SO₄, followed by filtration. The filtrate was concentrated under reduced pressure to yield a solid. The solid was purified by silica gel chromatography (eluent was changed from CH₂Cl₂ to CH₂Cl₂/EtOAc=5/1) and recrystallization from MeOH (20 mL) to yield compound 7a in the form of yellow powder in 65% yield. The spectral data of compound 7a are as follows:

$R_f$=0.23 (CH₂Cl₂/EtOAc=20/1); ¹H NMR (400 MHz, CD₂Cl₂): δ=7.78•7.73 (m, 2H), 7.62-7.54 (m, 2H), 7.45 (td, J=7.2 Hz, J=2.0 Hz, 2H), 7.30-7.17 (m, 18H), 7.12 (dd, J=7.6 Hz, J=2.4 Hz, 1H), 7.02-6.98 (m, 6H), 6.87 (dd, J=8.4 Hz, J=1.6 Hz, 1H); ¹³C NMR (100 MHz, CDCl₃): δ=165.75 (d, J=20.6 Hz, C), 158.35 (d, J=9.9 Hz, C), 147.43 (s, C), 147.26 (s, C), 141.14 (s, C), 140.59 (s, C), 138.75 (d, J=103.7 Hz, C), 138.51 (d, J=19.8 Hz, C), 137.09 (d, J=108.6 Hz, C), 132.41 (br m, CH), 131.18 (d, J=11.6 Hz, C), 130.81 (d, J=10.7 Hz, CH), 130.04 (d, J=102.9 Hz, C), 129.49 (d, J=9.9 Hz, CH), 129.19 (s, CH), 128.98 (d, J=12.3 Hz, CH) 128.67 (s, CH), 128.57 (s, CH), 128.51 (s, CH), 128.24 (d, J=11.6 Hz, CH), 127.41 (s, CH), 124.46 (s, CH), 123.19 (s, CH), 122.45 (s, CH), 122.28 (s, CH), 120.05 (s, CH), 66.31 (d, J=11.9 Hz, C), the signal coupled with the signal at 123.07 ppm of the doublets of the carbon of CH, one doublet and two singlets of the carbon of CH could not be identified because they were overlapped with other signals; ³¹P NMR (162 MHz, CD₂Cl₂): δ=24.81; HRMS (APCI): m/z calcd. for C₄₅H₃₃NOP: 634.2294 ([M+H]⁺); found. 634.2302.

Compound 7b

Synthetic intermediate M10b was synthesized from starting materials of synthetic intermediate 9b (0.500 mmol) and 4,4'-bis(tri(ethylene glycol) monomethyl ether) benzophenone (0.600 mmol) in the similar manner as synthetic intermediate M10a. Compound 7b was synthesized in the similar manner as compound 7a, except that synthetic intermediate M10a was replaced with synthetic intermediate M10b. The spectral data of compound 7a are as follows:

$R_f$=0.38 (EtOAc); ¹H NMR (600 MHz, CDCl₃): δ=8.07 (d, J=12.1 Hz, 1H), 7.84-7.80 (m, 2H), 7.73 (d, J=7.9 Hz, 1H), 7.62 (d, J=8.0 Hz, 1H), 7.52 (t, J=7.3 Hz, 1H), 7.46-7.39 (m, 5H), 7.30-7.26 (m, 3H), 7.21-7.18 (m, 7H), 7.02-6.98 (m, 6H), 6.85-6.80 (m, 5H), 4.11-4.08 (m, 4H), 3.85-3.83 (m, 4H), 3.74-3.71 (m, 4H), 3.68-3.62 (m, 8H), 3.54-3.51 (m, 4H), 3.36 (s, 3H), 3.35 (s, 3H); ¹³C NMR (150 MHz, CDCl₃): δ=166.78 (d, J=18.5 Hz, C), 159.12 (d, J=9.9 Hz, C), 158.10 (s, C), 158.07 (s, C), 147.55 (s, C), 147.37 (s, C), 139.55 (d, J=103.6 Hz, C), 135.22 (s, C), 134.25 (d, J=21.0 Hz, C), 133.61 (s, C), 133.07 (s, C), 132.64 (d, J=12.3 Hz, C), 132.37 (d, J=2.5 Hz, CH), 131.06 (d, J=9.9 Hz, CH), 131.04 (d, J=11.1 Hz, C), 129.91 (s, CH), 129.75 (s, CH), 129.26 (s, CH), 129.08 (s, CH), 129.01 (d, J=12.5 Hz, CH), 128.92 (s, CH), 128.34 (s, CH), 127.04 (s, CH), 124.58 (s, CH), 123.24 (s, CH), 122.60 (s, CH), 122.23 (d, J=8.6 Hz, CH), 122.17 (s, CH), 119.85 (s, CH), 114.61 (s, CH), 114.54 (s, CH), 71.97 (s, CH), 70.86 (s, CH), 70.85 (s, CH), 70.71 (s, CH), 70.62 (s, CH), 69.73 (s, CH), 69.71 (s, CH), 67.43 (s, CH), 65.11 (d, J=9.9 Hz, C), 59.07 (s, CH), the signal coupled with the signal at 135.94 ppm of the doublets corresponding to quaternary carbon, the signal paired with the signal at 130.35 ppm of those doublets, the signal coupled with the signal at 131.18 ppm of the doublets corresponding to the carbon of aromatic CH, and five singlets corresponding to the carbon of aliphatic CH could not be identified because they were overlapped with other signals; $^{31}$P NMR (162 MHz, CDCl$_3$): δ=24.83; HRMS (APCI): m/z calcd. for $C_{63}H_{63}NO_9P$: 1008.4235 ([M+H]$^+$); found. 1008.4217.

3. Optical Properties

The optical properties of compounds 1 to 3, 6b to 6d, 7a, and 7b were evaluated. Ultraviolet-visible (UV-Vis) absorption and fluorescence spectra were measured with an UV-Vis-NIR spectrophotometer UV-3150 (Shimadzu) and a fluorescence spectrophotometer F-4500 (Hitachi), respectively. Absolute fluorescence quantum yield was determined with an absolute PL quantum yield measurement instruments C9920-02 or C11347-01 (Hamamatsu Photonics). Sample solutions of all the samples were prepared using spectral grade solvents purchased from Nacalai Tesque, and were each measured with a 1 cm square quartz cuvette. The concentrations of each sample for the measurement of UV-Vis absorption spectra were set for ca. 10$^{-5}$ M. The concentrations of each sample for the measurement of fluorescence spectra were adjusted in a range where concentration quenching would not occur. For the measurement of absolute fluorescence quantum yield, each sample solution was deaerated by purging with an argon gas stream for several minutes prior to the measurements. The results are shown in Tables 1 to 8. The orientation polarizabilities Δf of hexane, ethyl acetate, and methanol, which are not shown in the Tables, were −0.000518, 0.201, and 0.309, respectively.

As shown in Table 1, the fluorescence wavelength of compound 1 shifted to the longer wavelength with retaining the high absolute fluorescence quantum yields, as the polarity of the solvent increases. Compound 1 exhibited a high absolute fluorescence quantum yield even in ethanol. This is significantly different from the optical properties of known phosphole compounds. Known phosphole compounds exhibit strong fluorescence in low-polarity solvents, but do not in high-polarity protic solvents, such as ethanol. On the other hand, compound 1 exhibited strong fluorescence in various solvents from low-polarity to high-polarity solvents. According to the fact that compound 2, which is an analogue of compound 1 without a phenyl group at the 3-position of the benzophosphole, show similar optical properties to compound 1 as shown in Tables 1 and 2, the optical properties of phospholes turned out to be hardly affected by the substituent at the 3-position.

As shown in Tables 2 and 3, Compound 3, which is an analogue of compound 2 with a 4-(N,N-dimethylamino) phenyl group at the 2-position of the benzophosphole in place of 4-(N,N-diphenylamino)phenyl group in compound 2, exhibited similar fluorescence properties with compound 2, whereas compound 3 tends to exhibit a higher absolute fluorescence quantum yield than compound 2. Compounds 6b to 6d exhibited similar fluorescent properties to compound 1 as shown in Tables 4 to 6. Moreover, as shown in Tables 7 and 8, the 2-aminophenyl-substituted benzophosphole oxides with ring-fused structure that connects phosphole ring and the benzene ring of aniline moiety each other like the compounds 7a and 7b, has similar or superior fluorescent properties compared to those of compound 1.

TABLE 1

Compound 1

| | Solvent | | | | | | |
|---|---|---|---|---|---|---|---|
| | cyclohexane | benzene | CHCl$_3$ | CH$_2$Cl$_2$ | DMF | EtOH | CH$_3$CN |
| Orientation Polarizability of Solvent Δf | −0.00131 | 0.002998 | 0.148156 | 0.217117 | 0.274396 | 0.288735 | 0.304568 |
| Absorption Maximum Wavelength λ max/nm | 412 | 416 | 418 | 416 | 409 | 417 | 404 |
| Molar Absorption Coefficient ε/10$^4$M$^{-1}$ cm$^{-1}$ | 1.82 | 1.88 | 1.78 | 1.76 | 1.77 | 1.68 | — |
| Emission Maximum Wavelength λ em/nm | 508 | 531 | 551 | 561 | 598 | 595 | 597 |
| Fluorescence Quantum Yield φ$_F$ | 0.92[a,c] | 0.89[b] | 0.89[b] | 0.84[b] | 0.71[b] | 0.57[a] | 0.67[a] |

[a]Measurement was performed using the apparatus C11347-01.
[b]Measurement was performed using the apparatus C9920-02.
[c]Self-absorption correction was carried out on the basis of Reference 1(Rev. Sci. Instrum. 2007, 78, 086105.).

TABLE 2

Compound 2

|  | Solvent | | | | | |
|---|---|---|---|---|---|---|
|  | cyclohexane | benzene | $CH_2Cl_2$ | DMF | EtOH | $CH_3CN$ |
| Orientation Polarizability of Solvent Δf | −0.00131 | 0.002998 | 0.217117 | 0.274396 | 0.288735 | 0.304568 |
| Absorption Maximum Wavelength λ max/nm | 410 | 414 | 413 | 409 | 416 | 406 |
| Molar Absorption Coefficient $\epsilon/10^4 M^{-1} cm^{-1}$ | 1.95 | 1.91 | 1.75 | 1.71 | 1.78 | 1.77 |
| Emission Maximum Wavelength λ em/nm | 456 | 497 | 543 | 564 | 565 | 571 |
| Fluorescence Quantum Yield $\varphi_F{}^a$ | 0.93[b] | 0.97 | 0.91 | 0.67 | 0.57 | 0.61 |

[a] Measurement was performed using the apparatus C11347-01.
[b] Self-absorption correction was carried out on the basis of Reference 1(Rev. Sci. Instrum. 2007, 78, 086105.).

TABLE 3

Compound 3

|  | Solvent | | | | | |
|---|---|---|---|---|---|---|
|  | cyclohexane | benzene | $CH_2Cl_2$ | DMF | EtOH | $CH_3CN$ |
| Orientation Polarizability of Solvent Δf | −0.00131 | 0.002998 | 0.217117 | 0.274396 | 0.288735 | 0.304568 |
| Absorption Maximum Wavelength λ max/nm | 401 | 410 | 412 | 412 | 415 | 408 |
| Molar Absorption Coefficient $\epsilon/10^4 M^{-1} cm^{-1}$ | — | 1.89 | 1.71 | 1.73 | 1.69 | 1.73 |
| Emission Maximum Wavelength λ em/nm | 456 | 507 | 532 | 559 | 565 | 558 |
| Fluorescence Quantum Yield $\varphi_F{}^a$ | 0.91[b] | 0.95 | 0.93 | 0.88 | 0.82 | 0.89 |

[a] Measurement was performed using the apparatus C11347-01.
[b] Self-absorption correction was carried out on the basis of Reference 1(Rev. Sci. Instrum. 2007, 78, 086105.).

TABLE 4

Compound 6b

|  | Solvent | | | |
| --- | --- | --- | --- | --- |
|  | cyclohexane | CH$_2$Cl$_2$ | EtOH | CH$_3$CN |
| Absorption Maximum Wavelength λ max/nm | 409 | 414 | 413 | 405 |
| Molar Absorption Coefficient ε/10$^4$M$^{-1}$ cm$^{-1}$ | 4.17 | 3.66 | 2.67 | 3.25 |
| Emission Maximum Wavelength λ em/nm | 450 | 533 | 550 | 563 |
| Fluorescence Quantum Yield φ$_F$[a] | 0.90 | 0.95 | 0.79 | 0.80 |

[a]Measurement was performed using the apparatus C11347-01.

TABLE 5

Compound 6c

|  | Solvent | | | |
| --- | --- | --- | --- | --- |
|  | cyclohexane | ethyl acetate | EtOH | CH$_3$CN |
| Absorption Maximum Wavelength λ max/nm | 420 | 420 | 429 | 425 |
| Molar Absorption Coefficient ε/10$^4$M$^{-1}$ cm$^{-1}$ | 2.38 | 2.38 | 2.33 | 2.35 |
| Emission Maximum Wavelength λ em/nm | 466 | 538 | 583 | 580 |
| Fluorescence Quantum Yield φ$_F$[a] | 0.90 | 0.90 | 0.67 | 0.71 |

[a]Measurement was performed using the apparatus C11347-01.

TABLE 6

Compound 6d

|  | Solvent | | | |
| --- | --- | --- | --- | --- |
|  | cyclohexane | ethyl acetate | EtOH | CH$_3$CN |
| Absorption Maximum Wavelength λ max/nm | 440 | 436 | 448 | 439 |
| Molar Absorption Coefficient ε/10$^4$M$^{-1}$ cm$^{-1}$ | 1.81 | 2.02 | 1.94 | 2.07 |
| Emission Maximum Wavelength λ em/nm | 495 | 564 | 611 | 620 |
| Fluorescence Quantum Yield φ$_F$[a] | 0.92 | 0.90 | 0.51 | 0.58 |

[a]Measurement was performed using the apparatus C11347-01.

TABLE 7

Compound 7a

|  | Solvent | | | |
| --- | --- | --- | --- | --- |
|  | cyclohexane | ethyl acetate | EtOH | CH$_3$CN |
| Absorption Maximum Wavelength λ max/nm | 424 | 424 | 439 | 428 |
| Molar Absorption Coefficient ε/10$^4$M$^{-1}$ cm$^{-1}$ | 1.60 | 1.61 | 1.60 | 1.62 |
| Emission Maximum Wavelength λ em/nm | 482 | 540 | 589 | 590 |
| Fluorescence Quantum Yield φ$_F$[a] | 0.88 | 0.90 | 0.70 | 0.79 |

[a]Measurement was performed using the apparatus C11347-01.

TABLE 8

Compound 7b

|  | Solvent | | | | |
| --- | --- | --- | --- | --- | --- |
|  | cyclohexane | CH$_2$Cl$_2$ | EtOH | CH$_3$CN | MeOH |
| Absorption Maximum Wavelength λ max/nm | 422 | 430 | 433 | 423 | 433 |
| Molar Absorption Coefficient ε/10$^4$M$^{-1}$ cm$^{-1}$ | 2.16 | 2.33 | 2.34 | 2.34 | 2.24 |

TABLE 8-continued

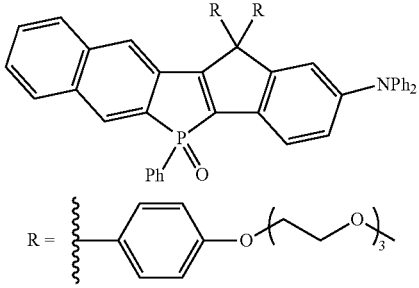

Compound 7b

| | Solvent | | | | |
|---|---|---|---|---|---|
| | cyclohexane | $CH_2Cl_2$ | EtOH | $CH_3CN$ | MeOH |
| Emission Maximum Wavelength $\lambda$ em/nm | 471 | 542 | 562 | 569 | 579 |
| Fluorescence Quantum Yield $\varphi_F{}^a$ | 0.91 | 0.92 | 0.91 | 0.90 | 0.74 |

[a]Measurement was performed using the apparatus C11347-01.

4. Solvent Effect on Optical Properties

The relationships between the orientation polarizability $\Delta f$ of the solvent and the Stokes shift of Compounds 1 to 3 were obtained from the results shown in Tables 1 to 3. The results are shown in FIG. 1. The orientation polarizability $\Delta f$ was calculated by using the equation shown in FIG. 1 using the dielectric constant $\in$ and refractive index n of the solvents. The Stokes shift is defined as the energy difference (unit: $cm^{-1}$) between the emission and the absorption maximum, and is calculated using the emission maximum wavelengths $\lambda$em and absorption maximum wavelengths $\lambda$max after the conversion to the corresponding energy unit in $cm^{-1}$. FIG. 1 clearly showed linear relationships between the Stokes shift in compounds 1 to 3 and the orientation polarizability $\Delta f$. Thus, if any of compounds 1 to 3 is used as a fluorescent dye, the orientation polarizability $\Delta f$ can be defined based on a Stokes shift derived from the measurement of $\lambda$max and $\lambda$em. In other words, the polarity of the environment around the fluorescent dye can be derived from the Stokes shift.

5. Cell Staining Experiments (1) Cell Staining Experiment with Compound 1

In 10 mM aqueous solution of compound 1 containing 0.1% of dimethyl sulfoxide, HeLa cells were cultured at 37° C. for 24 hours. The cells were washed with 3% sucrose aqueous solution and observed under a microscope. For the observation, ZEISS confocal microscope system (LSM 780) was used. As a result, the entire cell compartments except nuclei were stained. Fluorescent spectra were measured for each pixel and were fitted into three different fluorescence components with emission maximum wavelengths of 530 nm, 550 nm, and 565 nm, respectively. The portions around the surfaces of the cells exhibited luminescence with an emission maximum of mainly 530 nm, and the cytoplasm exhibited luminescence with an emission maximum of 565 nm. In the cytoplasm, many portions with an emission maximum at 550 nm were also observed. These results are probably due to the varied luminescent colors dependent on the polar environment of the stained cell tissue, and thus suggests that imaging of intracellular environment is possible with a single compound 1.

(2) Cell Staining Experiment with Compound 3

In 100 nM aqueous solution of compound 3 containing 0.001% of dimethyl sulfoxide, HeLa cells were cultured at 37° C. for one hour. The cells were washed with 3% sucrose aqueous solution and observed under a microscope. For the observation, ZEISS confocal microscope system (LSM 780) was used. As a result, the entirety of the cells except nuclei was stained. Fluorescent spectra were measured for each pixel and were fitted into two different fluorescence spectra with emission maximum wavelengths of 520 nm and 570 nm, respectively. These results show that the emission wavelength varies depending on the stained site.

6. Photobleaching Resistance

Figure 2:
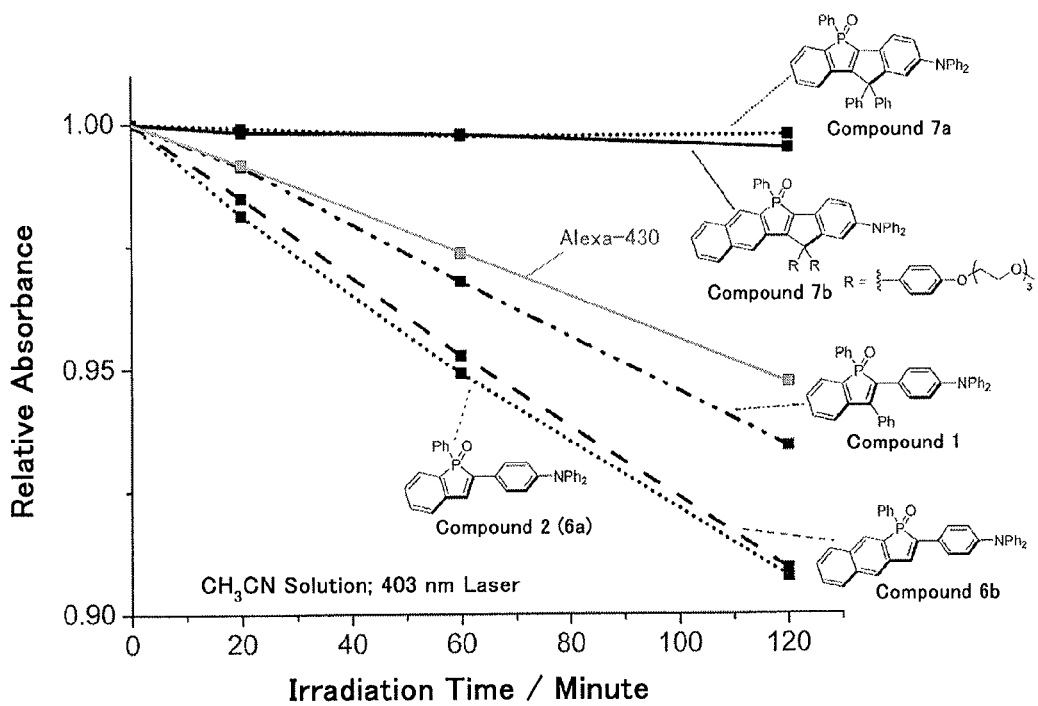
FIG. 2 is a graph showing the relationships between irradiation time and relative absorbance.

Solutions of compounds 1, 2 (6a), 6b, 7a, 7b, and a known fluorescent dye Alexa-430 each in acetonitrile were prepared so that their absorbances are in the range from 0.39 to 0.44. The concentration of each compound in the solution was $2.35 \times 10^{-5}$ M for compound 1, $2.17 \times 10^{-5}$ M for compound 2 (6a), $1.25 \times 10^{-5}$ M for compound 6b, $3.30 \times 10^{-5}$ M for compound 7a, and $2.04 \times 10^{-5}$ M for compound 7b. Alexa-430 is known as a highly photostable fluorescent dye. Immediately after preparation of each acetonitrile solution, the molar absorption coefficient of the acetonitrile solution was measured. Then, the molar absorption coefficient of the acetonitrile solution was measured after each of irradiations with 403 nm laser light for 20 minutes, 60 minutes, and 120 minutes, and the relative absorbance was determined relative to the molar absorption coefficient before laser light irradiation (immediately after preparation of the solution). The results are shown in FIG. 2. As shown in FIG. 2, compounds 7a and 6b exhibited an outstanding resistance to photobleaching with retaining the relative absorbance almost quantitatively even after irradiation with laser light for 120 minutes, compared to compounds 1, 2 (6a), 6b, and fluorescent dye Alexa-430.

The present invention is not limited the examples described above. It will be appreciated that the present invention can be implemented in various forms so long as they fall within the technical scope of the invention.

The present application claims priority from Japanese Patent Application No. 2014-11473 filed on Jan. 24, 2014, the entire contents of which are incorporated herein by reference.

INDUSTRIAL APPLICABILITY

The present invention can be used in the chemical industry, for example, as a luminescent material of organic EL elements or in a fluorescent dye for biological fluorescent imaging.

The invention claimed is:

1. A phosphole compound represented by the following formula (2):

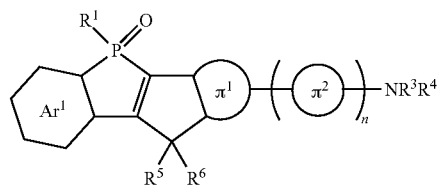

wherein in formula (2), $R^1$ represents an aryl group or a substituted aryl group; $R^3$ and $R^4$ are the same and are each an alkyl group, a substituted alkyl group, an aryl group, or a substituted aryl group; $R^5$ and $R^6$ are the same and are each an alkyl group, a substituted alkyl group, an aryl group, or a substituted aryl group; Ar represents a hydrocarbon aromatic ring or a substituted hydrocarbon aromatic ring; n is 0; $\pi^1$ is a benzene ring; and —$NR^3R^4$ is located at the 5- or the 6-position of the indene ring.

2. The phosphole compound according to claim 1, wherein Ar is a benzene ring or a naphthalene ring.

3. The phosphole compound according to claim 2, wherein $R^3$ and $R^4$ are each an alkyl group or a substituted alkyl group.

4. A fluorescent dye containing the phosphole compound according to claim 1.

\* \* \* \* \*